(12) United States Patent
Wolff et al.

(10) Patent No.: US 6,740,643 B2
(45) Date of Patent: May 25, 2004

(54) COMPOSITIONS AND METHODS FOR DRUG DELIVERY USING AMPHIPHILE BINDING MOLECULES

(75) Inventors: Jon A. Wolff, Madison, WI (US); James E. Hagstrom, Madison, WI (US); Sean D. Monahan, Madison, WI (US); Vladimir Budker, Middleton, WI (US); David B. Rozema, Madison, WI (US); Paul M. Slattum, Madison, WI (US)

(73) Assignee: Mirus Corporation, Madison, WI (US)

( * ) Notice: Subject to any disclaimer, the term of this patent is extended or adjusted under 35 U.S.C. 154(b) by 102 days.

(21) Appl. No.: 09/726,792

(22) Filed: Nov. 29, 2000

(65) Prior Publication Data

US 2001/0044412 A1 Nov. 22, 2001

Related U.S. Application Data

(63) Continuation-in-part of application No. 09/234,606, filed on Jan. 21, 1999, now abandoned.
(60) Provisional application No. 60/167,836, filed on Nov. 29, 1999.

(51) Int. Cl.$^7$ .............................................. A61K 48/00
(52) U.S. Cl. ........................ 514/44; 424/450; 424/486
(58) Field of Search .............................. 424/450, 486; 435/320.1, 455, 458; 514/44

(56) References Cited

U.S. PATENT DOCUMENTS

| 5,759,573 A | * | 6/1998 | Kim ........................... 424/450 |
| 6,022,737 A | * | 2/2000 | Niven et al. ............. 435/320.1 |
| 6,048,736 A | * | 4/2000 | Kosak ........................ 436/536 |

FOREIGN PATENT DOCUMENTS

| WO | WO 96/08235 | * | 3/1996 |
| WO | WO 97/04747 | * | 2/1997 |
| WO | WO 97/161169 | * | 5/1997 |
| WO | WO 99/12523 | * | 3/1999 |

OTHER PUBLICATIONS

Lawrencia et al. Gene Therapy. 2001, vol. 8, pp. 760–768.*
Danko, I., et al., "High Expression of Naked Plasmid DNA in Muscles of Young Rodents." *Human Molecular Genetics*; 1997; vol. 6, No. 9; pp. 1435–1443.
Felgner, Philip L., et al., "Lipofection: A Highly Efficient, Lipid–Mediated DNA–Transfection Procedure." *Biochemistry*; Nov. 1987; vol. 84; pp. 7413–7417.
Gonzalez, Hector, et al., "New Class of Polymers for the Delivery of Macromolecular Therapeutics." *Bioconjugate Chem.*; 1999; vol. 10; pp. 1068–1074.
Kamata, Hideaki, et al., "Amphiphilic Peptides Enhance the Efficiency of Liposome–Mediated DNA Transfection." *Nucleic Acids Research*; 1994; vol. 22, No. 3; pp. 536–537.
Kichler, Antoine, et al., "Efficient Gene Delivery With Neutral Complexes of Lipospermine and Thiol–Reactive Phospholipids." *Biochemical and Biophysical Research Communications*; Apr. 17, 1995; vol. 209, No. 2; pp. 444–450.
Legendre, Jean–Yves, et al., "Delivery of Plasmid DNA Into Mammalian Cell Lines Using pH–Sensitive Liposomes: Comparison With Cationic Liposomes." *Pharmaceutical Research*; 1992; vol. 9, No. 10; pp. 1235–1241.
Remy, Jean–Serge, et al., "Gene Transfer With a Series of Lipophilic DNA–Binding Molecules." *Bioconjugate Chem.*; 1994; vol. 5; pp. 647–654.
Remy, Jean–Serge, et al., "Targeted Gene Transfer Into Hepatoma Cells With Lipopolyamine–Condensed DNA Particles Presenting Galactose Ligands: A Stage Toward Artificial Viruses." *Biochemistry*; Feb. 1995; vol. 92; pp. 1744–1748.
Stella, Valentino J., et al., "Cyclodextrins: Their Future in Drug Formulation and Delivery." *Pharmaceutical Research*; 1997; vol. 14, No. 5; pp. 556–567.
Wagner, Ernst, et al., "Delivery of Drugs, Proteins and Genes Into Cells Using Transferrin as a Ligand For Receptor–Mediated Endocytosis." *Advanced Drug Delivery Reviews*; 1994; vol. 13; pp. 113–135.
Zhou, Xiaohuai, et al., "DNA Transfection Mediated by Cationic Liposomes Containing Lipopolylysine: Characterization and Mechanism of Action." *Biochimica et Biophysica Acta*; 1994; vol. 1189; pp. 195–203.
Zhou, Xiaohuai, et al., "Lipophilic Polylysines Mediate Efficient DNA Transfection in Mammalian Cells." *Biochimica et Biophysica Acta*; 1991; vol. 1065; pp. 8–14.

* cited by examiner

*Primary Examiner*—Dave Trong Nguyen
(74) *Attorney, Agent, or Firm*—Mark K. Johnson

(57) ABSTRACT

The present invention relates to the delivery of desired compounds (e.g., nucleic acids) into cells using noncovalent delivery systems which include complexing nucleic acids, amphipathic binding agents, and amphiphiles.

15 Claims, No Drawings

SEQUENCE LISTING

```
<160> NUMBER OF SEQ ID NOS: 9

<210> SEQ ID NO 1
<211> LENGTH: 14
<212> TYPE: PRT
<213> ORGANISM: Simian virus 40

<400> SEQUENCE: 1

Cys Gly Tyr Gly Pro Lys Lys Lys Arg Lys Val Gly Gly Cys
1               5                   10

<210> SEQ ID NO 2
<211> LENGTH: 13
<212> TYPE: PRT
<213> ORGANISM: Simian virus 40

<400> SEQUENCE: 2

Cys Gly Tyr Gly Pro Lys Lys Lys Arg Lys Val Gly Gly
1               5                   10

<210> SEQ ID NO 3
<211> LENGTH: 39
<212> TYPE: PRT
<213> ORGANISM: Simian virus 40

<400> SEQUENCE: 3

Cys Lys Lys Lys Ser Ser Ser Asp Asp Glu Ala Thr Ala Asp Ser Gln
1               5                   10                  15

His Ser Thr Pro Pro Lys Lys Lys Arg Lys Val Glu Asp Pro Lys Asp
            20                  25                  30

Phe Pro Ser Glu Leu Leu Ser
        35

<210> SEQ ID NO 4
<211> LENGTH: 37
```

```
<212> TYPE: PRT
<213> ORGANISM: Simian virus 40

<400> SEQUENCE: 4

Cys Lys Lys Lys Trp Asp Asp Glu Ala Thr Ala Asp Ser Gln His Ser
 1               5                  10                  15

Thr Pro Pro Lys Lys Arg Lys Val Glu Asp Pro Lys Asp Phe Pro
            20                  25                  30

Ser Glu Leu Leu Ser
        35

<210> SEQ ID NO 5
<211> LENGTH: 31
<212> TYPE: PRT
<213> ORGANISM: M9

<400> SEQUENCE: 5

Cys Tyr Asn Asp Phe Gly Asn Tyr Asn Asn Gln Ser Ser Asn Phe Gly
 1               5                  10                  15

Pro Met Lys Gln Gly Asn Phe Gly Gly Arg Ser Ser Gly Pro Tyr
            20                  25                  30

<210> SEQ ID NO 6
<211> LENGTH: 10
<212> TYPE: PRT
<213> ORGANISM: E1A

<400> SEQUENCE: 6

Cys Lys Arg Gly Pro Lys Arg Pro Arg Pro
 1               5                  10

<210> SEQ ID NO 7
<211> LENGTH: 22
<212> TYPE: PRT
<213> ORGANISM: Nucleoplasmin

<400> SEQUENCE: 7

Cys Lys Lys Ala Val Lys Arg Pro Ala Ala Thr Lys Lys Ala Gly Gln
 1               5                  10                  15

Ala Lys Lys Lys Lys Leu
            20

<210> SEQ ID NO 8
<211> LENGTH: 14
<212> TYPE: PRT
<213> ORGANISM: c-myc

<400> SEQUENCE: 8

Cys Lys Lys Lys Gly Pro Ala Ala Lys Arg Val Lys Leu Asp
 1               5                  10

<210> SEQ ID NO 9
<211> LENGTH: 21
<212> TYPE: PRT
<213> ORGANISM: Artificial Sequence
<220> FEATURE:
<223> OTHER INFORMATION: amphipathic alpha helical peptide

<400> SEQUENCE: 9

Lys Leu Leu Lys Leu Leu Leu Lys Leu Trp Leu Lys Leu Leu Lys Leu
 1               5                  10                  15

Leu Leu Lys Leu Leu
```

COMPOSITIONS AND METHODS FOR DRUG DELIVERY USING AMPHIPHILE BINDING MOLECULES

This application claims priority benefit of provisional application No. 60/167,836, filed on Nov. 29$^{th}$, 1999.

This application is a continuation-in-part of application Ser. No. 09/234,606 filed on Jan. 21, 1999 now abandoned.

FIELD OF TEHE INVENTION

The present invention relates to the delivery of desired compounds (e.g., drugs and nucleic acids) into cells using noncovalent delivery systems. The present invention provides compositions and methods for the delivery and release of a compound of interest to a cell.

BACKGROUND

Drup Delivery

A variety of methods and routes of administration have been developed to deliver pharmaceuticals that include small molecular drugs and biologically active compounds such as peptides, hormones, proteins, and enzymes to their site of actionl Parenter routes of administration include intravascular (intravenous, intraarterial), intramuscular, intraparenchymal, intradermal, subdermal, subcutareous, intratumor, intraperitoneal, and intralymphatic injections that use a syringe and a needle or catheter. The blood circulatory system provides systemic spread of the pharmaceutical. Polyethylene glycol and other hydrophilic polymers have provided proection of the pharmaceutical in the blood stream by preventing its interaction with blood components and to increase the circulatory time of the pharmaceutical by preventing opsonization , phagocytosis and uptake by the reticuloendothelial system. For example, the enzyme adenosine deaminase has been covalently modified with polyethylene glycol to incse the circulatory time and persistence of this enzyme in the treatment of patients with adenosine deaminase deficiency.

The controlled release of pharmaceuticals after their administration is under intensive development. Pharmaceuticals have also been complexed with a variety of biologically-labile polymers to delay their release from depots. These polymers have included copolymers of poly (lactic/glycolic acid) (PLGA) (Jain, R et al. Drug Dev. Ind. Pharm. 24, 703–727 (1998), ethylvinyl acetate/polyvinyl alcohol (Metrikin, DC and Anand, R, Curr Opin Ophthalmol 5, 21–29, 1994) as typical examples of biodegradable and non-degradable sustained release systems respectively.

Transdermal routes of administration have been effected by patches and ionotophoresis. Other epithelial routes include oral, nasal, respiratory, and vaginal routes of administration. These routes have attracted particular interest for the delivery of peptides, proteins, hormones, and cytokines which are typically administered by parenteral routes using needles. For example, the delivery of insulin via respiratory, oral, or nasal routes would be very attractive for patients with diabetes mellitas. For oral routes, the acidity of the stomach (pH less than 2) is avoided for plsensitive compounds by concealing peptidase-sensitive polypeptides inside phsensitive hydrogel matrix (copolymers of polyethyleneglycol and polyacrylic acid). After passing low pH compartments of gastrointestinal tract such structures swells at higher pH releasing thus a bioactive compound (Lowman AM et al. J. Pharm. Sci. 88, 933–937 (1999). Capsules have also been developed that release their contents within the small intestine based upon pH-dependent solubility of a polymer. Copolymers of polymethacrylic acid (Eudragit S, Rohm America) are known as polymers which are insoluble at lower pH but readily solubilinee at higher pH, so they are used as enteric coatings (Z Hu etal. J. Drug Target., 7, 223, 1999).

Biologically active molecules may be assisted by a reversible formation of covalent bonds. Quite often, it is found that the drug administered to a patient is not the active form of the drug, but is what is a called a prodrug that changes into the actual biologically active compound upon interactions with specific enzymes inside the body. In particular, anticancer drugs are quite toxic and are administered as prodrugs which do not become active until they come in cortact with the cancerous cell (Sezaki, II., Takakura, Y., Hashida, M. Adv. Drug. Delivery Reviews 3, 193, 1989).

Recent studies have found that pH in solid tumors is 0.5 to 1 units lower than in normal tissue (Gerweck LE et al. Cancer Res. 56, 1194 (1996). Hence, the use of pH-sensitive polymers for tumor targeting is justified. However, this approach was demonstrated only in vitro (Berton, M, Eur. J. Pharm. Biopharm. 47, 119–23, 1999).

Liposomes were also used as drug delivery vehicles for low molecular weight drugs and macromolecules such as amphotericin B for systemic fungal infections and candidiasis. Inclusion of anticancer drugs such as adriamycin have been developed to increase their delivery to tumors and reduce it to other tisue sites (e.g. heart) thereby decreasing their toxicity, pH-sensitive polymers have been used in conjunction with liposomes for the triggered release of an encapsulatede drug. For example, hydrophobically-modified N-isopropylacrylaride-methacrylic acid copolymer can render regular egg phosphatidyl chloline liposomes pH-sensitive by ph-dependent interaction of grafted aliphatic chains with lipid bilayer (O Meyer et al., FEBS Lett., 421, 61, 1998).

Gene And Nucleic Acid-Based Delivery

Gene or polynucleotide transfer is the cardinal process of gene therapy. The gene needs to be transferred across the cell membrane and enter the nucleus where the gene can be expressed. Gene transfer methods currently being explored included viral vectors and physical-chemical methods.

Viruses have evolved over millions of year to transfer their genes into mammalian cells. Viruses can be modified to carry a desired gene and become a "vector" for gene therapy. Using standard recombinant techniques, the harmful or superfluous viral genes can be removed and replaced with the desired normal gene. This was first accomplished with mouse retroviruses. The development of retroviral vectors were the catalyst that promoted current gene therapy efforts. However, they cannot infect all cell types very efficiently, especially in vivo. Other viral vectors based on Herpes virus are being developed to enable more efficient gene transfer into brain cells. Adenoviral and adenoassociated vectors are being developed to infect lung and other cells.

Besides using viral voctors, it is possible to directly transfer genes into mammalian cells. Usually, the desired gene is placed within bacterial plasmid DNA along with a mammalian promoter, enhancer, and other sequences that enable the gene to be expressed in mammalian cells. Several milligrams of the plasmid DNA containing all these sequences can be prepared and purified from the bacterial cultures. The plasmid DNA containing the desired gene can be incorporated into lipid vesicles (liposomes including cationic lipids such as Lipofectin) that then transfer the plasmid DNA into the target cell. Plasmid DNA can also be complexed with proteins that target the plasniid DNA to specific tissues just as certain proteins are taken up (endocytosed) by specific cells. Also, plasmid DNA can be complexed with polymers such as polylysine and polyethylenimine. Another plasmid-based technique involves "shooting" the plasmid DNA on small gold beads into the cell using a "gun". Finally, muscle cells in vivo have the unusual ability to take up and express plasmid DNA.

Gene therapy approaches can be clsssified into direct and indirect methods. Some of these gene transfer methods are most effective when directly injected into a tissue space. Direct methods using many of the above gene transfer techniques are being used to target tumors, muscle, liver, lung, and brain. Other methods are most effective when applied to cells or tissues that have been removed from the body and the genetically-modified cells are then transplanted back into the body. Indirect approaches in conjunction with retroviral vectors are being developed to transfer genes into bone marrow cells, lymphocytes, hepatocytes, myoblasts and skin cells.

Gene Therapy And Nucleic Acid-Based Therapies

Gene therapy promises to be a revolutionary advance in the treatment of disease. It is a fundamentally new approach for treating disease that is different from the conventional surgical and pharmaceutical therapies. Conceptually, gene therapy is a relatively simple approach. If someone has a defective gene, then gene therapy would fix the defective gene. The disease state would be modified by manipulating genes instead of their products, i.e proteins, enzymes, enzyme substrates and enzyme products. Although, the initial motivation for gene therapy was the treatment of genetic disorders, it is becoming increasingly apparent that gene therapy will be useful for the treatment of a broad range of acquired diseases such as cancer, infectious disorders (AIDS), heart disease, arthritis, and neurodegenerative disorders (Parkinson's and Alzheimer's).

Gene therapy promises to take fulladvantage of the major advances brought about by molecular biology. While, biochemistry is mainly concerned with how the cell obtains the energy and matter that is required for normal function, molecular biology is mainly concerned with how the cell gets the information to perform its fiuctions. Molecular biology wants to discover the flow of information in the cell. Using the metaphor of computers, the cell is the hardware while the genes are the software. In this sense, the purpose of gene therapy is to provide the cell with a new program (genetic information) so as to reprogram a dysfunctional cell to perform a normal function. The addition of a new cellular function is provided by the insertion of a foreign gene that expresses a foreign protein or a native protein at amounts that are not present in the patient.

The inhibition of a cellular function is provided by anti-sense approaches (that is acting against messenger RNA) and that includes oligonuclcotides complementary to the messenger RNA sequence and ribozymes. Messenger RNA (mRNA) is an intermediate in the expression of the DNA gene. The MRNA is translated into a protein. "Anti-sense" methods use a RNA sequence or an oligonucleotide that is made complementary to the target mRNA sequence and therefore binds specifically to the target messenger RNA. When this anti-sense sequence binds to the target mRNA, the mRNA is somehow destroyed or blocked from being translated. Ribozymes destroy a specific mRNA by a different mebcanism. Ribozymes are RNA's that contain sequence complementary to the target messenger RNA plus a RNA sequence that acts as an enzyme to cleave the messenger RNA, thus destroying it and preventing it from being translated. When these anti-sense or ribozyme sequences are introduced into a cell, they would inactivate their specific target mRNA and reduce their disease-causing properties.

Several recessive genetic disorders are being considered for gene therapy. One of the first uses of gene therapy in humans has been used for the genetic deficiency of the adenosine deaminase (ADA) gene. Other clinical gene therapy trials have been conducted for cystic fibrosis, familial hypercholesteremia caused by a defective LDL-receptor gene and partial ornithine transcarbomylase deficiency. Both indirect and direct gene therapy approaches are being developed for Duehenne muscular dystrophy. Patients with this type of muscular dystrophy eventually die from loss of their respiratory muscles. Direct approaches include the intramuscular injection of naked plasmid DNA or adenoviral vectors.

A wide variety of gene therapy approaches for cancer are under investigation in animals and in human clinical trials. One approach is to express in lymphocytes and in the tumor cells, cytokine genes that stimulate the immune system to destroy the cancer cells. The cytokine genes would be transferred into the lymphocytes by removing the lymphocytes from the body and infecting them with a retroviral vector carrying the cytokine gene. The tumor cells would be similarly genetically modified by this indirect approach to express cytokines within the tumor. Direct approaches involving the expression of cytokines in tumor cells in situ are also being considered. Other genes besides cytolines may be able to induce an immune response against the cancer. One approach that has entered clinical trials is the direct injection of HLA-B7 gene (which encodes a potent immunogen) within lipid vesicles into malignant melanomas in order to induce a more effective immune response against the cancer.

"Suicide" genes are genes that KiU cells that express the gene. For example, the diphtheria toxin gene directly kills cells. The Herpes thymidine kinase (TK) gene kills cells in conjunction with acyclovir (a drug used to treat Herpes viral infections). Other gene therapy approaches take advantage of our knowledge of oncogenes and suppressor tumor genes also known as anti-oncogenes. The loss of a functioning anti-oneogene plays a decisive role in childhood tumors such as retinoblastoma, osteosarcoma and Wilms tumor and may play an important role in more common tumors such as lung, colon and breast cancer. Introduction of the normal anti-oncogene back into these tumor cells may convert them back to normal cells. The activation of oncogenes also plays an important role in the development of cancers. Since these oncogenes operate in a "dominant" fashion, treatment will require inactivation of the abnormal oncogene. This can be done using either "anti-sense" or ribozyme methods that selectively inactivate a specific messenger RNA in a cell.

Gene therapy can be used as a type of vaccination to prevent infectious diseases and cancer. When a foreign gene is trammferred into a cell and the protein is made, the foreign protein is presented to the immune system differently from simply injecting the foreign protein into the body. This different presentation is more likely to cause a cell mediated immune response which is important for fighting latent viral infections such as human immunodeficiency virus (HIV causes AIDS), Herpes and cytomegalovirus. Expression of the viral gene within a cell simulates a viral infection and induces a more effective immune response by fooling the body that the cell is actually infected by the virus, without the danger of an actual viral jinection.

One direct approach uses the direct intramuscular injection of naked plasmid DNA to express a viral gene in muscle cells. The "gun" has also been shown to be effective at inducing an immune response by expressing foreign genes in the skin. Other direct approaches involving the use of retroviral, vaccinia or adenoviral vectors are also being developed. An indirect approach has been developed to remove fibroblasts from the skin, infect them with a retroviral vector carrying a viral gene and trsplant the cells back into the body. The envelope gene from the AIDS virus (HIV) is often used for these purposes. Many cancer cells express specific geres that normal cells do not Therefore, these genes specifically expressed in cancer cells can be used for immunization against cancer.

Besides the above immunization approaches, several other gene therapies are being developed for treating infectious disease. Most of these new approaches are being developed for HIV infection and AIDS. Many of them will involve the delivery of anti-sense or ribozyme sequences directed against the particular viral messenger RNA. These anti-sense or ribozyme sequences will block the expression of specific viral genes and abort the viral infection without damaging the infected cell. Another approach somewhat similar to the anti-sense approaches is to overexpress the target sequences for these regulatory HIV sequences.

Gene therapy efforts would be directed at lowering the risk factors associated with atherosclerosis. Overexpression of the LDL receptor gene would lower blood cholesterol in patients not only with familial hypercholesterernia but with other causes of high cholesterol levels. The genes encoding the proteins for HDL ("the good cholesterol") could be expressed also in various tissues. This would raise HDL levels and prevent atherosclerosis and heart attacks. Tissue plasminogen activator (tPA) protein is being given to patients inmediately after their myocardial infarction to digest the blood clots and open up the blocked coronary blood vessels. The gene for tPA could be expressed in the endothelial cells lining the coronary blood vessels and thereby deliver the tPA locally without providing tPA throughout the body. Another approach fbr coronary vessel disease is to express a gene in the heart that produces a protein that causes new blood vessels to grow. This would increase collateral blood flow and prevent a myocardial infarction from occurring.

Neurodegenerative disorders such as Parkinson's and Alzheimer's diseases are good candidates for early attempts at gene therapy. Arthritis could also be treated by gene therapy. Several proteins and their genes (such as the IL-1 receptor antagonist protein) have recently been discovered to be anti-inflammatory. Expression of these genes in joint (synovial) fluid would decrease the joint inflammation and treat the arthritis.

In addition, methods are being developed to directly modify the sequence of target genes and chromosomal DNA. The delivery of a nucleic acid or other compound that modifies the genetic instruction (e.g., by homologous recombination) can correct a mutated gene or mutate a functioning gene.

Polymers for Drug and Nucleic Acid Delivery

Polymers are used for drug delivery for a variety of therapeutic purposes. Polymers have also been used in research for the delivery of nucleic acids (polynucleotides and oligonucleotides) to cells with an eventual goal of providing therapeutic processes. Such processes have been termed gene therapy or anti-sense therapy. One of the several methods of nucleic acid delivery to the cells is the use of DNA-polycation complexes. It has been shown that cationic proteins like histones and protamines or synthetic polymers like polylysine, polyarginine, polyornithine, DEAE dextaan, polybrene, and polyethylenimine may be effective intracellular delivery agents while small polycations like spermine are ineffective. The following are some important principles involving the mechanism by which polycations facilitate uptake of DNA:

Polycations provide attachment of DNA to the cell surface. The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis. Furthermore, polycations are a convenient linker for attaching specific ligands to DNA and as result, DNA-polycation complexes can be targeted to specific cell types.

Polycations protect DNA in complexes against nuclease degradation. This is important for both extra- and intracellular preservation of DNA. Gene expression is also enabled or increased by preventing endosome acidification with $NH_4Cl$ or chloroquine. Polyethylenimine, which facilitates gene expression without additional treatrments, probably disrupts endosomal function itself. Disruption of endosormnal function has also been accomplished by linking to the polycation endosomal-disruptive agents such as fusion peptides or adenoviruses.

Polycations can also facilitate DNA condensation. The volume which one DNA molecule occupies in a complex with polycatioms is drastically lower than the volume of a free DNA molecule. The size of a DNA/polymer complex is probably critical for gene delivery in vivo. In terms of intravenous injection, DNA needs to cross the endothelial barrier and reach the parenchymal cells of interest. The largest endothelia fenestrae (holes in the endothelial barrier) occur in the liver and have an average diameter of 100 nm. The trans-epithelial pores in other organs are much smaller, for example, muscle endothelium can be described as a structure which has a large number of small pores with a radius of 4 nm, and a very low number of large pores with a radius of 20–30 nm. The size of the DNA complexes is also important for the cellular uptake process. After binding to the cells the DNA—polycation complex should be taken up by endocytosis. Since the endocytic vesicles have a homogenous internal diameter of about 100 nm in hepatocytes and are of similar size in other cell types, DNA complexes smaller than 100 nm are preferred.

Condensation of DNA

A significant number of multivalent cations with widely different molecular structures have been shown to induce condensation of DNA.

Two approaches for compacting (used herein as an equivalent to the term condensing) DNA:

1. Multivalent cations with a charge of three or higher have been shown to condense DNA. These include spermidine, spermine, $Co(NH_3)_6^{3+}$, $Fe^{3+}$, and natural or synthetic polymers such as histone HI, protarnitie, polylysine, and polyethylenimine. Analysis has shown DNA condensation to be favored when 90%/ or more of the charges along the sugar-phosphate backbone are neutralized.
2. Polymers (neutral or anionic) which can increase repulsion between DNA and its surroundings have been shown to compact DNA. Most significantly, spontaneous DNA selfassembly and aggregation process have been shown to result from the confinement of large amounts of DNA, due to excluded volume effect.

Depending upon the concentration of DNA, condensation leads to three main types of structures:

1) In extremely dilute solution (about 1 ug/mL or below), long DNA molecules can undergo a monomolecular collapse and form structures described as toroid.

2) In very dilute solution (about 10 ug/mL) microaggregates form with short or long molecules and remain in suspension. Toroids, rods and small aggregates can be seen in such solution.

3) In dilute solution (about 1 mg/mL) large aggregates are formed that sediment readily.

Toroids have been considered an attractive form for gene delivery because they have the smallest size. While the size of DNA toroids produced within single preparations has been shown to vary considerably, toroid size is unaffected by the length of DNA being condensed. DNA molecules from 400 bp to genomic length produce toroids similar in size. Therefore one toroid can include from one to several DNA molecules. The kinetics of DNA collapse by polycations that resulted in toroids is very slow. For example DNA condensation by $Co(NH_3)_6Cl_3$ needs 2 hours at room temperature.

The mechanism of DNA condensation is not clear. The electrostatic force between unperturbed helices arises primarily from a counterion fluctuation mechanism requiring multivalent cations and plays a major role in DNA condensation. The hydration forces predominate over electrosatic forces when the DNA helices approach closer then a few water diameters. In a case of DNA—polymeric polycation interactions, DNA condensation is a more complicated process than the case of low molecular weight polycations. Different polycationic proteins can generate toroid and rod formation with different size DNA at a ratio of positive to negative charge of two to five. T4 DNA complexes with polyarginine or histone can form two types of structures; an elongatd structure with a long axis length of about 350 nm (like free DNA) and dense spherical particles. Both forms exist simultaneously in the same solution. The reason for the co-existence of the two forms can be explained as an uneven distribution of the polycation chains among the DNA molecules. The uneven distribution generates two thermodynamically favorable conformations.

The electrophoretic mobility of DNA—polycation complexes can change from negative to positive in excess of polycation. It is likely that large polycations do not completely align along DNA but form polymer loops that interact with other DNA molecules. The rapid aggregation and strong intermolecular forces between different DNA molecules may prevent the slow adjustment between helices needed to form tightly packed orderly particles.

As previously stated, preparation of polycation-condensed DNA particles is of particular importance for gene therapy, more specifically, particle delivery such as the design of non-viral gene transfer vectors. Optimal transfection activity in vitro and in vivo can require an excess of polycation molecules. However, the presence of a large excess of polycations may be toxic to cells and tissues. Moreover, the non-specific binding of cationic particles to all cells forestalls cellular targeting. Positive charge also has an adverse influence on biodistribution of the complexes in vivo.

Several modifications of DNA-cation particles have been created to circumvent the nonspecific interactions of the DNA-cation particle and the toxicity of cationic particles. Examples of these modifications include attachment of steric stabilizers, e.g. polyethylene glycol, which inhibit non-specific interactions between the cation and biological polyanions. Another example is reclarging the DNA particle by the additions of polyanions, which interact with the cationic particle, thereby lowering its surface charge, i.e. recharging of the DNA particle U.S. Ser. No. 09/328,975. Another example is cross-linking the polymers and thereby caging the complex described in U.S. Ser. No. 08/778,657, U.S. Ser. No. 09/000,692, U.S. Ser. No. 09/070299, and U.S. Ser. No. 09/464,871. Nucleic acid particles can be formed by the formation of chemical bonds and template polymerization described in U.S. Ser. No. 08/778,657, U.S. Ser. No. 09/000,692, U.S. Ser. No. 09/070299, and U.S. Ser. No. 09/464,871.

A potential problem with these modifications is that they may be irreversible rendering the particle unable to interact with the cell to be transfected, and/or incapable of escaping from the lysosome once taken into a cell, and/or incapable of entering the nucleus once inside the cell. A method for formation of DNA particles that is reversible under conditions found in the cell may allow for effective delivery of DNA. The conditions that cause the reversal of particle formation may be, but not limited to, the pH, ionic strength, oxidative or reductive conditions or agents, or enzymatic activity.

DNA Template Polymerization

Low molecular weight cations with valency <+3 fail to condense DNA in aqueous solutions under normal conditions. However, cationic molecules with the charge <+3 can be polymerized in the presence of DNA and the resulting polymers can cause DNA to condense into compact structures. Such an approach is known in synthetic polymer chemistry as template polymerization. During this process, monomers (which are initially weakly associated with the template) are positioned along template's backbone, thereby promoting their polymerization. Weak elecrostatic association of the nascent polymer and the template becomes stronger with chain growth of the polymer. Trubetskoy et al used two types of polymerization reactions to achieve DNA condensation: step polymerization and chain polymerization (V S Trubetskoy, V G Budker, L J Hanson, P M Slattum, J A Wolff, L E Hagstrom. Nucleic Acids Res. 26:4178–4185, 1998) U.S. Ser. No. 08/778,657, U.S. Ser. No. 09/000,692, U.S. Ser. No. 97/24089, U.S. Ser. No. 09/070299, and U.S. Ser. No. 09/464,871. Bis(2-aminoethyl)-1,3-propanediamine (AEPD), a tetraamine with 2.5 positive charges per molecule at pH 8 was polymerized in the presence of plasmid DNA using cleavable disulfide amino-reactive cross-linkers dithiobis (succinimidyl propionate) and dimethyl-3,3'-dithiobispropionimidate. Both reactions yielded DNA/polymer complexes with significant retardation in agarose electrophoresis gels demonstrating significant binding and DNA condensation. Treatment of the polymerized complexes with 100 mM dithiothreitol (DTT) resulted in the pDNA returning to its normal supercoiled position following electrophoresis proving thus cleavage the backbone of the The template dependent polymerization process was also tested using a 14 mer peptide encoding the nuclear localizing signal (NLS) of SV40 T antigen (CGYGPKKKRKVGGC) as a cationic "macromonomer". Other studies included pegylated comonomer (PEG-AEPD) into the reaction mixture and resulted in "worm"-like structures (as judged by transmission electron microscopy) that have previously been observed with DNA complexes formed from block copolymers of polylysine and PEG (M A Wolfert, E H Schacht, V Toncheva, K Ulbrich, O Nazarova, L W Seymour Human Gene Ther. 7:2123–2133, 1996). Blessing et al used bisthiol derivative of spermine and reaction of thio-disulfide exchange to promote chain growth. The presence of DNA accelerated the polymerization reaction as measured the rate of disappearance of free thiols in the reaction mixture (T Blessing, J S Remy, J P Behr. J. Am. Chem. Soc. 120:8519–8520, 1998).

"Caging" of Polycation-condensed DNA Particles

The stability of DNA nanoassemblies based on DNA condensation is generally low in vivo because they easily engage in polyion exchange reactions with strong polyanions. The process of exchange consists of two stages: 1) rapid formation of a triple DNA-polycation-polyanion complex, 2) slow substitution of one same-charge polyion with another. At equilibrium conditions, the whole process eventually results in formation of a new binary complex and an excess of a third polyion. The presence of low molecular weight salt can greatly accelerate such exchange reactions, which ofen result in complete disassembly of condensed DNA particles. Hence, it is desirable to obtain more colloidally stable structures where DNA would stay in its condensed form in complex with corresponding polycation independently of environment conditions.

The complete DNA condensation upon neutralization of only 90% of the polymer's phosphates results in the presence of unpaired positive charges in the DNA particles. If the polycation contains such reactive groups, such as primary amines, these unpaired positive charges may be modified. This modification allows practically limitless possibilities of modulating colloidal properties of DNA particles via chemical modifications of the complex. We have demonstrated the utility of such reactions using traditional DNA-poly-L-lysine (DNA/PLL) system reacted with the cleavable cross-linking reagent dimethyl-3,3'-dithiobispropionimidate (DTBP) which reacts with primary amino groups with formation of amidines (V S Trubetskoy, A Loomis, P M Slattutn, J E Hagstrom, V G Budker, J A Wolff. Bioconjugate Chem. 10:624–628, 1999) U.S. Ser. No. 08/778,657, U.S. Ser. No. 09/000,692, U.S. Ser. No. 97/24089, U.S. Ser. No. 09/070299, and U.S. Ser. No. 09/464,871. Similar results were achieved with other polycations including poly (allylamine) and histone H1. The use of another bifunctional reagent, glutaraldehyde, has been described for stabilization of DNA complexes with cationic peptide CWK18 (R C Adam, K G Rice. J. Pharm. Sci. 739–746,1999).

Recharging

The caging approach described above could lead to more colloidally stable DNA assemblies. However, this approach may not change the particle surface charge. Caging with bifunctional reagents, which preserve positive charge of amino group, keeps the particle positive. However, negative surface charge would be more desirable for many practical applications, i.e. in vivo delivery. The phenomenon of surface recharging is well known in colloid chemistry and is described in great detail for lyophobic/lyophilic systems (for example, silver halide hydrosols). Addition of polyion to a suspension of latex particles with oppositely-charged surface leads to the permanent absorption of this polyion on the surface and, upon reaching appropriate stoichiometry, changing the surface charge to opposite one. This whole process is salt dependent with flocculation to occur upon reaching the neutralization point.

We have demonstrated that similar layering of polyelectrolytes can be achieved on the surface of DNA/polycation particles (VS Trubetskoy, A Loomis, J E Hagstrom, V G Budker, J A Wolff. Nucleic Acids Res. 27:3090–3095, 1999). The principal DNA-polycation (DNA/pC) complex used in this study was DNA/PLL (1:3 charge ratio) formed in low salt 25 mM HEPES buffer and recharged with increasing amounts of various polyanions. The DNA particles were characterized after addition of a third polyion component to a DNA/polycation complex using a new DNA condensation assay (V S Trubetskoy, P M Slattum, J E Hagstrom, J A Wolff, V G Budker. Anal. Biochem. 267:309–313, 1999) and static light scattering. It has been found that certain polyanions such as poly(methacrylic acid) and poly(aspartic acid) decondensed DNA in DNA/PLL complexes. Suprisingly, polyanions of lower charge density such as succinylated PLL and poly(glutamic acid), even when added in 20-fold charge excess to condensing polycation (PLL) did not decondense DNA in DNA/PLL (1:3) complexes. Further studies have found that displacement effects are sal-dependent. In addition, polyglutamnate but not the relatively weaker polyanion succinylated poly-L-lysine (SPLL) displaces DNA at higher sodium chloride concentrations. Measurement of z-potential of DNA/PLL particles during titration with SPLL revealed the change of particle surface charge at approximately the charge equivalency point. Thus, it can be concluded that addition of low charge density polyanion to the cationic DNA/PLL particles results in particle surface charge reversal while maintaining condensed DNA core intact. Finally, DNA/polycation complexes can be both recharged and crosslinked or caged U.S. Ser. No. 08/778,657, U.S. Ser. No. 09/000,692, U.S. Ser. No. 97/24089, U.S. Ser. No. 09/070299, and U.S. Ser. No. 09/464,871.

The Use of pH-Sensitive Lipids, Amphipathic Compounds, and Liposomes for Drug and Nucleic Acid Delivery After the landmark description of DOTMA (N-[1-(2,3-dioleyloxy)propyl]-N,N,N-trimethylammonium chloride) [Felgner, P L, Gadek, T R, Holm, M, et al. Lipofection: a highly efficient, lipid-mediated DNAtransfection procedure. Proc. Natl. Acad Sci. USA. 1987;84:7413–7417], a plethora of cationic lipids have been synthesized. Basically, all the cationic lipids are amphipathic compounds that contain a hydrophobic domain, a spacer, and positively-charged amine. The hydrophobic domains are typically hydrocarbon chains such as fatty acids derived from oleic or myristic acid. The hydrocarbon chains are often joined either by ether or ester bonds to a spacer such as glycerol. Quaternary amines often compose the cationic groups. Usually, the cationic lipids are mixed with a fusogenic lipid such as DOPE (dioleoyl phosphatidyl ethanolamine) to form liposomes. The mixtures are mixed in chloroform that is then dried. Water is added to the dried lipid film and unilamellar liposomes form during sonication. Multilamellar cationic liposomes and cationic liposomes/DNA complexes prepared by the reverse-phase evaporation method have also been used for tnansfection. Cationic liposomes have also been prepared by an ethanol injection technique.

Several cationic lipids contain a spennine group for binding to DNA. DOSPA, the cationic lipid within the LipofectAMINE formulation (Life Technologies) contains a spermine linked via a amide bond and ethyl group to a trimethyl, quaternary amine [Hawley-Nelson, P, Ciccarone, V and Jessee, J. Lipofectnine reagent: A new, higher efficiency polycationic liposome transfection reagent. Focus 1993;15:73–79]. A French group has synthesized a series of cationic lipids such as DOGS (dioctadecylglycinespermine)

that contain spermine [Remy, J-S, Sirlin, C, Vierling, P, et al. Gene transfer with a series of lipophilic DNA-binding molecules. *Bioconjugate Chem.* 1994;5:647–654]. DNA has also been transfected by lipophilic polylysines which contain dipalmotoylsuccinylglycerol chemically-bonded to low molecular weight (~3000 MW) polylysine [Zhou, X, Kilbanov, A and Huang, L Lipophilic polylysines mediate efficient DNA transfection in mammalian cells. *Biochim. Biophys. Acta* 1991;1065:8–14. Zhou, X and Huang, L. DNA transfection mediated by cationic liposomes containing lipopolylysine: Characterization and mechanism of action. *Biochim. Biophys. Acia* 1994;1195–203].

Other studies have used adjuvants with the cationic liposomes. Transfection efficiency into Cos cells was increased when amphiphilic peptides derived from influenza virus hemagglutinin were added to DOTMA/DOPE Iposomes [Kamata, H, Yagisawa, H, Takahashi, S, et al. Amphiphilic peptides enhance the efficiency of liposome-mediated DNA transfection. *Nucleic Acids Res.* 1994;22:536–537]. Cationic lipids have been combined with galactose ligands for targeting to the bepatocyte asialoglycoprotein receptor [Remy, J-S, Kichler, A, Mordvinov, V, et al. Targeted gene transfer into hepatoma cells with lipopolyamine-condensed DNA particles presenting galactose ligands: A stage toward artificial viruses. *Proc. Natl. Acad. Sci USA* 1995;92:1744–1748]. Thiol-reactive phospholipids have also been incorporated into cationic lipid/pDNA complexes to enable cellular binding even when the net charge of the complex is not positive [Kichier, A, Remy, J-S, Boussif, O, et al. Efficient gene delivery with neutral complexes of lipospermine and thiol-reactive phospholipids. *Biochem. Biophys. Res. Comm.* 1995;209:444–450]. DNA-dependent template process converted thiol-containing detergent possessing high critical micelle concentration into dimeric lipid-like molecule with apparently low water solubility (JP Behr and colleagues).

Cationic liposomes may deliver DNA either directly across the plasma membrane or via the endosome compartment. Regardless of its exact entry point, much of the DNA within cationic liposomes does accumulate in the endosome compartment. Several approaches have been investigated to prevent loss of the foreign DNA in the endosomal compartment by protecting it from hydrolytic digestion within the endosomes or enabling its escape from endosomes into the cytoplasm. They include the use of acidotropic (lysomotrophic), weak amines such as chloroquine that presumably prevent DNA degradation by inhibiting endosomal acidification [Legendre, J. & Szoka, F. Delivery of plasmid DNA into mammalian cell lines using pH-sensitive liposomes: Comparison with cationic liposomes. *Pharmaceut. Res.* 9, 1235–1242 (1992)]. Viral fusion peptides or whole virus have been included to disrupt endosomes or promote fusion of liposomes with endosomes, and facilitate release of DNA into the cytoplasm [Kamata, H., Yagisawa, H., Takahashi, S. & Hirata, H. Amphiphilic peptides enhance the efficiency of liposome-mediated DNA transfection. *Nucleic Acid Res.* 22, 536–537 (1994). Wagner, E., Curiel, D. & Cotten, M. Delivery of drugs, proteins and genes into cells using transferrin as a ligand for receptor-mediated endocytosis. *Advanced Drug Delivery Reviews* 14, 113–135 (1994)].

Knowledge of lipid phases and membrane fusion has been used to design potentially more versatile liposomes that exploit the endosomal acidification to promote fusion with endosomal membranes. Such an approach is best exemplified by anionic, pH-sensitive liposomes that have been designed to destabilize or fuse with the endosome membrane at acidic pH [Duzgunes, N., Straubinger, R. M., Baldwin, P. A. & Papahadjopoulos, D. *PH-sensinve liposomes.* (eds Wilschub, J. & Hoekstra, D.) p. 713–730 (Marcel Deker INC, 1991)]. All of the anionic, pHensitive liposomes have utilized phosphatidylethanola mine (PE) bilayers that are stabilized at non-acidic pH by the addition of lipids that contain a carboxylic acid group. Liposomes containing only PE are prone to the inverted hexagonal phase ($H_{II}$). In pH-sensitive, anionic liposomes, the carboxylic acid's negative charge increases the size of the lipid head group at pH greater than the carboxylic acid's pK and thereby stabilizes the phosphatidylethanolamine bilayer. At acidic pH within endosomes, the uncharged or reduced charge species is unable to stabilize the phosphatidylethanolamine-rich bilayer. Anionic, pgsensitive liposomes have delivered a variety of membrane-impermeant compounds including DNA. However, the negative charge of these pH-sensitive liposomes prevents them from efficiently taking up DNA and interacting with cells; thus decreasing their utility for transfection. We have described the use of cationic, pH-sensitive liposomes to mediate the efficient transfer of DNA into a variety of cells in culture U.S. Ser. No. 08/530, 598, and U.S. Ser. No. 09/020,566.

The Use of pH-Sensitive Polymers for Drug and Nucleic Acid Delivery

Polymers that pH-sensitive are have found broad application in the area of drug delivery exploiting various physiological and intracellular pH gradients for the purpose of controlled release of drugs (both low molecular weight and polymeric). pH sensitivity can be broadly defined as any change in polymer's physico-chemical properties over certain range of pH. More narrow definition demands significant changes in the polymer's ability to retain (release) a bioactive substance (drug) in a physiologically tolerated pH range (usually pH 5.5–8). pH-sensitivity presumes the presence of ionizable groups in the polymer (polyion). All polyions can be divided into three categories based on their ability to donate or accept protons in aqueous solutions: polyacids, polybases and polyampholytes. Use of pH-sensitive polyacids in drug delivery applications usually relies on their ability to become soluble with the pH increase (acid/salt conversion), to fam complex with other polymers over change of pH or undergo significant change in hydrophobicity/hydrophilicity balance. Combinations of all three above factors are also possible.

Copolymers of polymethacrylic acid (Eudragit S, Rohbn America) are known as polymers which are insoluble at lower pH but readily solubilized at higher pH, so they are used as enteric coatings designed to dissolve at higher intestinal pH (Z Hu et al. *J. Drug Target.*, 7, 223, 1999). A typical example of pH-dependent complexation is copolymers of polyacrylate(graft)ethyleneglycol which can be formulated into various pH-sensitive hydrogels which exhibit pH-dependent swelling and drug release (F Madsen et al., *Biomaterials*, 20, 1701, 1999). Hydrophobically-modified N-isopropylacrylamide-methacrylic acid copolymer can render regular egg PC liposomes pH-sensitive by pH-dependent interaction of grafted aliphatic chains with lipid bilayer (O Meyer et al., *FEBS Lett.*, 421, 61, 1998). Polymers with pH-mediated hydrophobicity (like polyethylacrylic acid) can be used as endosomal disruptors for cytoplasmic drug delivery (Murthy, N., Robichaud, J. R, Tirrell, D. A., Stayton, P. S., Hofflman, A. S. *J. Controlled Release* 61, 137, 1999).

Polybases have found broad applications as agents for nucleic acid delivery in transfection/gene therapy applications due to the fact they are readily interact with polyacids. A typical example is polyethylenimine (PEI). This polymer secures nucleic acid electrostatic adsorption on the cell surface followed by endocytcsis of the whole complex. Cytoplasmic release of the nucleic acid occurs presumably via the so called "proton sponge" effect according to which pH-sensitivity of PEI is responsible for endosome rupture due to osmotic swelling during its acidification (O Boussif et aL Proc. Natl. Acad. Sci. USA 92, 7297, 1995). Cationic acrylates possess the similar activity (for example, poly-((2-dimethylarnino)ethyl methacrylate) (P van de Wetering et al. J. Controlled Release 64, 193, 2000). However, polybases due to ther polycationic nature pH-sensitive polybases have not found broad in vivo application so far, due to their acute systemic toxicity in vivo (JH Senior, Biochim. Biophys. Acta, 1070, 173, 1991). Milder polybases (for example, linear PEI) are better tolerated and can be used systemically for in vivo gene transfer (D Goula et al. Gene Therapy 5, 712, 1998).

Endosome Disruption

Many biologically active compounds, in particular large and/or charged compounds, are incapable of crossing biological membranes. In crder for these compounds to enter cells they must either be taken up by the cells via endocytosis, into endosomes, or there must be a disruption of the cellular membrane to allow the compound to cross. In the case of endosomal entry, the endosomal membrare must be disrupted to allow for the entrance of the compound in the enterior of the cell. Therefore, either entry pathway into the cell requires a disruption of the cellular membrane. There exist compounds termed membrane active compounds that disrupt membranes. One can imagine that if the membrane active agent were operative in a certain time and place it would facilitate the tansport of the biologically active compound across the biological membrane. The control of when and where the membrane active compound is active is crucial to effective transport. If the membrane active compound is too active or active at the wrong time, then no transport occurs or transport is associated with cell rupture and thereby cell death. Nature has evolved various strategies to allow for membrane transport of biologically active compounds including membrane fusion and the use membrane active compounds whose activity is modulated such that activity assists transport without toxicity. Many lipid-based transport formulations rely on membrane fusion and some membrane active peptides' activities are modulated by pH. In particular, viral coat proteins are ofben pH-sensitive, inactive at neutral or basic pH and active under the acidic conditions found in the endosome.

Small Molecular Endosomolytic Agents

A cellular transport step that has attracted attention for gene transfer is that of DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. A number of chemicals such as chloroquine, bafilomycin or Brefeldin A1 have been used to disrupt or modify the trafficking of molecules through intracellular pathways. Chloroquine decreases the acidification of the endosomal and lysosomal compartments but also affects other cellular functions. Brefeldin A, an isoprenoid fungal metabolite, collapses reversibly the Golgi apparatus into the endoplasmic reticulum and the early endosomal comparunent into the trans-Golgi network (TGN) to form tubules. Bafilomycin $A_1$, a macrolide antibiotic is a more specific inhibitor of endosomal acidification and vacuolar type $H^+$—ATPase than chloroquine.

Viruses, Proteins and Peptides for Disruption of Endosomes and Endosomal Function Viruses such as adenovirus have been used to induce gene release from endosomes or other intracellular compartments (D. Curiel, Agarwal, S., Wagner, E., and Cotten, M. PNAS 88:8850, 1991). Rhinovirus has also been used for this purpose (W. Zauner et al. J. Virology 69:1085–92, 1995). Viral components such as influenza virus hemagglutinin subunit HA-2 analogs has also been used to induce endosomal release (E. Wagner et al. PNAS 89:7934, 1992). Amphipathic peptides resembling the Nterminal HA-2 sequence has been studied (K. Mechtler and E. Wagner, New J. Chem. 21: 105–111, 1997). Parts of the pseudonmonas exotoxin and diptheria toxin have also been used for drug delivery (I. Pastan and D. FitzGerald. J. Biol. Chem. 264:15157, 1989).

A variety of synthetic amphipathic peptides have been used to enhance transfection of genes (N. Ohmori et al. Biochem. Biophys. Res. Commun. 235:726, 1997). The ER-retaining signal (KDEL sequence) has been proposed to enhance delivery to the endoplasmic reticulum and prevent delivery to lysosomes (S. Seethararn et al. J. Biol. Chem. 266:17376, 1991). Other Cellular and Intracellular Gradcents Useful for Delivery Nucleic acid and gene delivery may involve the biological pH gradient that is active within organisms as a factor in delivering a polynucleotide to a cell. Different pathways that may be affected by the pH gradient include cellular transport mechanisms, endosomal disruption/breakdown, and particle disassembly (release of the DNA). Other gradients that can be useful in gene therapy research involve ionic gradients that are related to cells. For example, both $Na^+$ and $K^+$ have large concentration gradients that exist across the cell membrane. Systems containing metabinding groups can utilize such gradients to influence delivery of a polynucleotide to a cell. Changes in the osmotic pressure in the endosome also have been used to disrupt membranes and allow for transport across membrane layer. Buffering of the endosome pH may cause these changes in osmotic pressure. For example, the "proton sponge" effect of PEI (O Boussif et al. Proc. Natl. Acad. Sci. USA 92, 7297, 1995) and certain polyanions (Murthy, N., Robichaud, J. R., Tirrell, D. A., Stayton, P. S., Hoffmnan, A. S. Journal of Controlled Release 1999, 61, 137) are postulated to cause an increase in the ionic strength inside of the endosomc, which causes a increase in osmotic pressure. This pressure increase results in membrane disruption and release of the contents of the endosome.

In addition to pH and other ionic gradients, there exist other difference in the chemical environment associated with cellular activities that may be used in gene delivery. In particular enzymatic activity both extra and intraceuularly may be used to deliver the gene of interest either by aiding in the delivery to the cell or escape from intracellular compartments. Proteases, found in serum, lysosome and cytoplasm, may be used to disrupt the particle and allow its interaction with the cell surface or cause it fracture the intracellular compartment, e.g. endosome or lysosome, allowing the gene to be released intracellularly.

SUMMARY OF THE INVENTION

The invention relates to noncovalent amphiphile binding systems for use in biologic systems. More particularly, amphiphile-binding agents and polymers of amphiphile-binding agents are utilized in the delivery of molecules, polymers, nucleic acids and genes to cells.

Described in a preferred embodiment is a process for obtaining an expression product by delivering a polynucleotide to a cell, comprising the step of associating an amphiphile binding agent, an amphiphile, and a polynucleotide to form a complex. Then, delivering the complex to the cell and expressing the polynucleotide in the cell.

In another preferred embodiment, a complex is described for delivering and expressing DNA in a mammal, comprising an amphiphile binding agent, an amphiphile, and DNA in complex Another preferred embodiment is a process for obtaining an expression product in vivo, comprising forming a complex with a cyclodextrin, an amphiphile and a polynucleotide. Then, delivering the complex to a cell in a mammal which expresses the polynucleotide.

DETAILED DESCRIPTION OF THE INVENTION

The following description provides exemplary embodiments of the systems, compositions, and methods of the present invention. These embodiments include a variety of systems that have been demonstrated as effective delivery systems. The invention is not limited to these particular embodiments.

Cyclodextrin Structure and Binding Properties

Cyclodextrins are naturally occurring cyclic oligomers of glucose in 1–4 α linkages (structure 1).

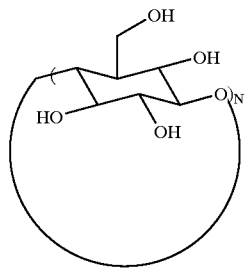

Cyclodextrin composed of six glucose units (N=6) is called α-cyclodextrin, 7 units is called β-cyclodextrin, and 8 is called γ-cyclodextrin. The cyclic structure is torroidal in shape with the center of the torroid relatively nonpolar compared to water. For this reason, cyclodextrins will bind to nonpolar sections of amphipathic compounds, also known as amphiphilic compounds or amphiphiles, in water. Amphiphiles are compounds that contain both hydrophilic and hydrophobic functional groups. Examples include lipids, acyl-glycerol, sterols, polyethyleneglycol, and amino acids. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfirs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups. Amphipathic compounds bound by cyclodextrins include hydrophobic amino acids (e.g. leucine and phenylalanine), surfactants (e.g. sodium dodecylsulfate and Triton X-100), and lipids (e.g.palmitic acid). The strength of the interaction between cyclodextrin and an amphiphilic compound depends on the size of both the hydrophobic part of the amphiphile and the cyclodextrin. For example, α-cyclodextrin will bind linear alkyl chains, but not branched tertiary alkyl groups, which are bound by β-cyclodextrin (Stella, V. J., Rajewsci, R. A. *Pharm. Res.* 1997, 14, 556. Stella, V. J., Rao, V. M. Zannov, E. A., Zia, V. *Adv. Drug Del. Rev.* 1999, 36, 3.).

Nucleic Acid Delivery by Polycations and Cationic Lipids

There are many nonviaal nucleic acid complexes that have been shown to aid in delivery of DNA into cells. Nucleic acid includes DNA (plasmid DNA, anti-sense, oligonucleotides) and RNA (ribozymes, oligonucleotides, artificial messenger RNA). In general, these nonviral complexes may be grouped into two classes: cationic lipid complexes (lipoplexes) and cationic polymer (polyplexes) complexes. In either case, the polyanionic DNA is complexed with a cation. In lipoplexes, the cations are associated noncovalently by hydrophobic lipid-lipid interactions to form a polycation. In polymer complexes, the positive charges are attached covalently to form a polycation. Nucleic acids are delivered to cells for the purpose of gene therapy and anti-sense therapy.

Nucleic Acids Complexes Containing Cyclodextrins

As mentioned previously, cyclodextrins form complexes with amphipathic molecules that may be positively or negatively charged. Therefore, a polymer composed of cyclodextrins will become a polyion, a noncovalent amphiphilic electrolyte, when associated with a charged amphiphile. For example, association between a polymer composed of cyclodextrins and a cationic amphiphile will result in a polycation that may interact with DNA. In a preferred embodiment, a cyclodextrin-contaming polymers are constructed by reacting cyclodextrin with epichlorohydrin under alkaline conditions to produce cyclodextrin-epichlorohydrin copolymer. This cyclodextrin-epichlorohydrin copolymer, compacts pDNA upon addition of cations such as 1adamantanamine or 1-dodecylamine. The complex of cyclodextrin-epichlorohydrin copolymer and 1-adamanta amine or 1-dodecylamine is a cationic noncovalent amphiphilic polyelectrolyte, which is capable of condensing DNA. In addition, cationic amphiphiles that are polymers that are bound to monomeric or polymeric amphiphile binding agents may be used to compact DNA. Such DNA-containing complexes may be used for taansfection of cells.

Amphiphile binding agents may also be used to create anionic noncovalent amphiphilic polyclectrolytes. Association between a polymer composed of cyclodextrins and an anionic amphiphile will result in a polyanion that will interact with a positively-charged DNA-polycation complex, i.e. "recharge" the DNA complex. In a preferred embodiment, the complex between cyclodextrin-epichlorohydrin copolymer and 4-t-butylbenzoic acid, to form an anionic noncovalent amphiphilic polyelectrolyte, was added to particles of DNA and poly-L-lysine. The resulting particles were found to transfect cells in vitro. In addition, anionic amphiphiles that are polymers that are bound to monomeric or polymeric amphiphile binding agents may be used to "recharge" DNA particles. For example, succinyloleoylpoly-L-lysine is an anionic polymeric amphiphile which complexes with the amphiphile binding agent β-cyclodextrin and interacts ("recharges") a poly-L-lysine condensed DNA particle. The addition of the cyclodextrin increased the transfection of the recharged particle 33 fold over recharged particle in the absence of cyclodextrin.

Not only is the cycbodextrin the basis for the DNA-polyion interaction, but cyclodextrinbased polyions may have properties (e.g. surface charge and stability) different from standard polyions. In contrast to standard polyions, the polyions derived from cyclodextrin-containing polymers and charged amphiphiles are reversible. The existence of the polyion is dependent upon the concentration of the cyclodextrin-containing polymer and the charged amphiphile, such that the disruption of the polyion maybe trigger by simple dilution of either cyclodextrin or charged amphiphile.

Monomeric cyclodextrins may also be incorporated into nucleic acid complexes by association with amphiphile molecules in a DNA complex. In this case, the cyclodextxins are not the basis for the DNA-electrolyte interactions, but may be used to change the properties of the DNA-electrolyte complex, e.g. stability or surface charge. The addition of cyclodextrin into a DNA particle also adds hydrophilic, but not charged, moieties to the particle. Hydrophilic molecules (e.g. PEG) have been shown to increase solubility of DNA particles, decrease the surface charge and thereby increase their stability. Cyclodextrins have the ability to bind to other nonionic hydrophilic molecules such as PEG. Therefore, addition of PEG to a cyclodextrin-containing DNA particle will result in PEG-particle interactions, which may confer the particle with added stability. Unlike other examples of PEG stabilization of DNA particles, the interaction between DNA particle and PEG is transient and may release under dilute, delivery conditions. The rate at which the PEG may be released may be altered by the number of PEG molecules incorporated, the number of cyclodextrins, and the incorporation of PEG derivatives with strong cyclodextrin binding regions (e.g. t-octylphenyl group of Triton X-100). In a preferred embodiment, addition of the PEG-derived detergent Triton X-100 to particles of DNA and poly-L-lysine-succinyl-β-cyclodextrin resulted in particles that were more stable than particles without addition of the Triton X-100.

Likewise, cell targeting ligands aid in transport to a cell but may not be necessary, and may inhibit, transport into a cell. In all of these cases, the reversible attachment of the interaction modifier, through a labile bond, would be beneficial.

The present invention provides for the transfer of polynucleotides, and other biologically active compounds into cells in culture (also known as "in vitro"). Compounds or kits for the tansfection of cells in culture is commonly sold as "transfection reagents" or "transfection kits". The present invention also provides for the transfer of polynucleotides, and biologically active compounds into cells within tissues in situ and in vivo, and delivered intravascurary (U.S. patent application Ser. No. 08/571, 536), intrarterially, intravenous, orally, intraduodenaly, via the jejunum (or ileum or colon), rectally, transdermally, subcutaneously, intramuscularly, intaaperitoraally, intraparenterally, via direct injections into tissues such as the liver, lung, heart, muscle, spleen, pancreas, brain (including intraventricular), spinal cord, ganglion, lymph nodes, lymphatic system, adipose tissues, thryoid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands. Compounds for the transfection of cells in vivo in a whole organism can be sold as "in vivo transfection reagents" or "in vivo transfection kits" or as a pharmaceutical for gene therapy.

Definitions

To facilitate an understanding of the present invention, a number of terms and phrases are defined below:

Amphliphile Binding Agent

Amphiphile binding agents are compounds with molecular weight 1,300 or less that bind through a noncovalent interaction amphiphilic compounds in water. The basis for this interaction is contact between hydrophobic portions of the amphiphile with hydrophobic portions of the amphiphile binding agent. In particular α, β and γ-cyclodextrins, and their derivatives, are amnphiphile binding agents.

Polymeric Amphiphile Binding Agent

Polyermic amphiphile binding agent is a polymer composed of monomers that are amphiphilc binding agents.

Noncovalent Amphiphilic Electrolytes

Noncovalent amphiphilic polyelectrolytes are systems composed of amphiphile binding agents and charged amphiphiles, which are bound by the amphiphile binding agents. The interaction between charged amphiphile and polymer results in a complex that has a different charge than the amphiphile binding agent alone. The amphiphile binding agent may be uncharged, charge positive or neutral, but upon interaction with a charged amphiphile the charge of the complex is different than the amphiphile binding agent alone.

Biologically Active Compound

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. In this specification, the cellular production of, a inhibition of a material, such as a protein, caused by a human assisting a molecule to an in vivo cell is an example of a delivered biologically active compound. Pharmaceuticals, proteins, peptides, polypeptides, enzyme inhibitors, hormones, cytokines, antigens, viruses, oligonucleotides, enzymes and nucleic acids are examples of biologically active compounds.

Peptide and Polypeptide

Peptide and polypeptide refer to a series of amino acid residues, more than two, connected to one another by amide bonds between the beta or alpha-amino group and carboxyl group of contiguous amino acid residues. The amino acids may be naturally occurring or synthetic. Polypeptide includes proteins and peptides, modified proteins and peptides, and non-natural proteins and peptides. Enzymes are proteins evolved by the cells of living organisms for the specific function of catalyzing chemical reactions. A chemical reaction is defined as the formation or cleavage of covalent or ionic bonds. Bioactive compounds may be used interchangeably with biologically active compound for purposes of this application.

Cyclodextrin

A cyclic oligomer of alpha-D-glucopyranose.

Delivery of Biologically Active Compound

The delivery of a biologically active compound is commonly known as "drug delivery". "Delivered" means that the biologically active compound becomes associated with the cell or organism. The compound can be in the circulatory system, intravessel, extracellular, on the membrane of the cell or inside the cytoplasm, nucleus, or other organelle of the cell.

Parenteral routes of administration include intravascular (intravenous, intraarterial), intramuscular, intraparenchymal, intradermal, subdermal, subcutaneous, intratumor, intraperitoneal, intrathecal, subdural, epidual, and intralymphatic injections that use a syringe and a needle or catheter. An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, and bile ducts. The intravascular route includes delivery through the blood vessels such as an artery or a vein. An administration route involving the mucosal membranes is meant to include nasal, bronchial, inhalation into the lungs, or via the eyes. Other routes of administration include intraparenchymal into tissues such as muscle (intramuscular), liver, brain, and kidney. Transdermal routes of administration have been effected by patches and ionotophoresis. Other epithelial routes include oral, nasal, respiratory, and vaginal routes of administration.

Delivery System

Delivery system is the means by which a biologically active compound becomes delivered. That is all compounds, including the biologically active compound itself, that are required for delivery and all procedures required for delivery including the form (such volume and phase (solid, liquid, or gas)) and method of administration (such as but not limited to oral or subcutaneous methods of delivery).

Nudeic Acid

The term "nucleic acid" is a term of art that refers to a polymer containing at least two nucleotides. "Nucleotides" contain a sugar deoxyribose (DNA) or ribose (RNA), a base, and a phosphate group. Nucleotides are linked together through the phosphate groups. "Bases" include purines and pyrimidines, which further include naturalcompounds adenine, thymine, guanine, cytosine, uracil, inosine, and natural analogs, and synthetic derivatives of punines and pyrimidines, which include, but are not limited to, modifications which place new reactive groups such as, but not limited to, aenines, alcohols, thiols, carboxylates, and alkylhalides. Nucleotides are the monomeric units of nucleic acid polymers. A "polynucleotide" is distinguished here from an "oligonucleotide" by containing more than 80 monomeric units; oligonucleotides contain from 2 to 80 nucleotides. The term nuclei acid includes deoxyribonucleic acid (DNA) and ribonucleic acid (RNA). The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

DNA may be in the form of anti-sense, plasmid DNA, parts of a plasmid DNA, product of a polymerase chain reaction (PCR), vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups.

"Anti-sense" is a polynucleotide that interferes with the function of DNA and/or RNA. This may result in suppression of expression. Natural nucleic acids have a phosphate backbone, artificial nucleic acids may contain other type of backbones and bases. These include PNAs (peptide nucleic acids), phosphothionates, and other variants of the phosphate backbone of native nucleic acids. In addition, DNA and RNA may be single, double, triple, or quadruple stranded.

The term "recombinant DNA molecule" as used herein refers to a DNA molecule that is comprised of segments of DNA joined together by means of molecular biological techniques. "Expression cassette" refers to a natural or recombinantly produced polynucleotide molecule that is capable of expressing protein(s). A DNA expression cassette typically includes a promoter (allowing transcription initiation), and a sequence encoding one or more proteins. Optionally, the expression cassette may include trancriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

A nucleic acid can be used to modify the genomic or extrachromosomal DNA sequences. This can be achieved by delivering a nucleic acid that is expressed. Alternatively, the nucleic acid can effect a change in the DNA or RNA sequence of the target cell. This can be achieved by homologous recombination, gene conversion, or other, yet to be described, mechanisms.

Gene

The term "gene" refers to a nucleic acid (e.g., DNA) sequence that comprises coding sequences necessary for the production of a polypeptide or precursor (e.g., —myosin heavy chain). The polypeptide can be encoded by a fiul length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends far a distance of about 1 kb or more on either end such that the gene corresponds to the length of the full-length mRNA. The sequences that are located 5' of the coding region and which are present on the mRNA are referred to as 5' nontranslated sequences. The sequences that are located 3' or downstream of the coding region and which are present on the mRNA are referred to as 3' non-trnslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript Alternatively, the coding region utilized in the expression vectors of the present invention may contain endogenous enhancers/promoters, splice junctions, intervening sequences, polyadenylation signals, etc. or a combination of both endogenous and exogenous control elements.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, nonisolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single tranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (ie., the oligonucleotide or polynucleotide may be double-stranded).

Gene Expression

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down regulation" or "repression" refers to regulation that decrease production. Molecules (e.g., transcription factors) that are involved in up-regulation or down-regulation are often called "activators" and "repressors," respectively.

Delivery of Nucleic Acids

The process of delivering a polynucleotide to a cell has been commonly termed "transfection" or the process of "transfecting" and also it has been termed "transformation". The polynucleotide could be used to produce a change in a cell that can be therapeutic. The delivery of polynucleotides or genetic material for therapeutic and research purposes is commonly called "gene therapy". The delivery of nucleic acid can lead to modification of the DNA sequence of the target cell.

The polynucleotides or genetic material being delivered are generally mixed with transfection reagents prior to delivery. The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the tranfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA. The term "naked polynucleotides" indicates that the polynucleotides are not associated with a transfection reagent or other delivery vehicle that is required for the polynucleotide to be delivered to a cell.

A "transfection reagent" or "delivery vehicle" is a compound or compounds that bind(s) to or complex(es) with oligonucleotides, polynucleotides, or other desired compounds and mediates their entry into cells. Examples of transfection reagents include, but are not limited to, cationic liposomes and lipids, polyamines, calcium phosphate precipitates, histone proteins, polyethylenimine, and polylysine complexes (polyethylenimine and polylysine are both toxic). Typically, when used for the delivery of nucleic acids, the transfection reagent has a net positive charge that binds to the polynucleotide's negative charge. For example, cationic liposomes or polylysine complexes have net positive charges that enable them to bind to DNA or RNA.

Enzyme

Enzyme is a protein that acts as a catalyst. That is a protein that increases the rate of a chemical reaction without itself undergoing any permanent chemical change. The chemical reactions that are catalyzed by an enzyme are termed enzymatic reactions and chemical reactions that are not are termed nonenzymnatic reactions.

Complex

Two molecules are combined, to form a complex through a process called complexation or complex formation, if the are in contact with one another through noncovalent interactions such as electrostatic interactions, hydrogen bonding interactions, and hydrophobic interactions.

Modification

A molecule is modified, to form a modification through a process called modification, by a second molecule if the two become bonded through a covalent bond. That is, the two molecules form a covalent bond between an atom from one molecule and an atom from the second molecule resulting in the formation of a new single molecule. A chemical covalent bond is an interaction, bond, between two atoms in which there is a sharing of electron density.

Osmosis

Osmosis is the passage of a solvent through a semipermeable membrane, a membrane through which solvent can pass but not all solutes, separating two solutions of different concentrations. There is a tendency for the separated solutions to become the same concentration as the solvent passes from low concentration to high concentration. Osmosis will stop when the two solutions become equal in concentration or when pressure is applied to the solution containing higher concentration. When the higher concentrated solution is in a closed system, that is when system is of constant volume, there is a build up of pressure as the solvent passes from low to high concentration. This build up of pressure is called osmotic pressure.

Salt

A salt is any compound containing ionic bonds, that is bonds in which one or more electrons are transferred completely from one atom to another.

Interpolyelectrolyte Complexes

An interpolyelectrolyte complexe is a noncovalent interaction between polyelectrolytes of opposite charge.

Charge, Polarity, and Sign

The charge, polarity, or sign of a compound refers to whether or not a compound has lost one or more electrons (positive charge, polarity, or sign) or gined one or more electrons (negative charge, polarity, or sign).

Cell Targeting Signals

Cell targeting signal (or abbreviated as the Signal) is defined in this specification as a molecule that modifies a biologically active compounds such as drug or nucleic acid and can direct it to a cell location (such as tissue) or location in a cell (such as the nucleus) either in culture or in a whole organism. By modifying the cellular or tissue location of the foreign gene, the function of the biologically active compound can be enhanced.

The cell targeting signal can be a protein, peptide, lipid, steroid, sugar, carbohydrate, (non-expresssing) polynucleic acid or synthetic compound. The cell targeting signal enhances cellular binding to receptors, cytoplasmic transport to the nucleus and nuclear entry or release from endosomes or other intracellular vesicles.

Nuclear localizing signals enhance the targeting of the pharmaceutical into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. These include a short NLS (H-CGYGPKKKRKVGG-OH) or long NLS's (H-CKKKSSSDDEATADSQHSTPPKKKRKVEDPKDF PSELLS-OH and H-CKKKWDDEATADSQHSTPPKKKRKVEDPKDFP SELLS-OH). Other NLS peptides have been derived from M9 protein (CYNDFGNYNNQSSNFGPMKQGNFGGRSSGPY), E1A (H-CKRGPKRPRP-OH), nucleoplasmin (H-CKKAVKRPAATKKAGQAKKKKL-OH),and c-myc (H-CKKKGPAAKRVKLD-OH).

Signals that enhance release from intracellular compartments (releasing signals) can cause DNA release from intracellular compartments such as endosomes (early and late), lysosomes, phagosomes, vesicle, endoplasrmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor signals are any signal that enhances the association of the biologically active compound with a cell. This can be accomplished by either increasing the binding of the compound to the cell surface and/or its association with an intracellular compartment, for example: ligands that enhance endocytosis by enhancing binding the cell surface. This includes agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as lipids, fatty acids, cholesterol, dansyl compounds, and amphotericin derivatives. In addition viral proteins could be used to bind cells.

Interaction Modifiers

An interaction modifier changes the way that a molecule interacts with itself or other molecules, relative to molecule containing no interaction modifier. The result of this modification is that self-interactions or interactions with other molecules are either increased or decreased. For example cell targeting signals are interaction modifiers that change the interaction between a molecule and a cell or cellular component Polyethylene glycol is an interaction modifier that decreases interactions between molecules and themselves and with other molecules.

Reporter or Marker Molecules

Reporter or marker molecules are compounds that can be easily detected. Typically they are fluorescent compounds such as fluorescein, rhodamine, Texas red, cy 5, cy 3 or dansyl compounds. They can be molecules that can be detected by infrared, ultraviolet or visible spectroscopy or by antibody interactions or by electron spin resonance. Biotin is another reporter molecule that can be detected by labeled avidin. Biotin could also be used to attach targeting groups.

Linkages

An attachment that provides a covalent bond or spacer between two other groups (chemical moieties). The linkage may be electronically neutral, or may bear a positive or negative charge. The chemical moieties can be hydrophilic or hydrophobic. Preferred spacer groups include, but are not limited to C1–C12 alkyl, C1–C12 alkenyl, C1–C12 alkynyl, C6–C18 aralkyl, C6–C18 aralkenyl, C6–C18 aralynyl, ester, ether, ketone, alcohol, polyol, amide, amine, polyglycol, polyether, polyamine, thiol, thio ether, thioester, phosphorous containing, and heterocyclic.

Bifunctional

Bifunctional molecules, commonly referred to as crosslinkers, are used to connect two molecules together, i.e. form a linkage between two molecules. Bifunctional molecules can contain homo or heterobifunctionality.

Crosslinking

Crosslinking refers to the chemical attachment of two or more molecules with a bifunctional reagent. A bifunctional reagent is a molecule with two reactive ends. The reactive ends can be identical as in a homobifunctional molecule, or different as in a heterobifucnctional molecule.

Amphiphilic and Amphipathic Compounds

Amphipathic, or amphiphilic, compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Detergent

Detergents or surfactants are water-soluble molecules containing a hydrophobic portion (tail) and a hydrophilic portion (head), which upon addition to water decrease water's surface tension. The hydrophobic portion can be alkyl, alkenyl, alkynyl or aromatic. The hydrophilic portion can be charged with either net positive (cationic detergents), negative (anionic detergents), uncharged (nonionic detergents), or charge neutral (zwitterionic detergent). Examples of anionic detergents are sodium dodecyl sulfate, glycolic acid ethoxylate(4 units) 4-tert-butylphenylether, palmitic acid, and oleic acid. Examples of cationic detergents are cetyltrimethylarmmonium bromide and oleylamine. Examples of nonionic detergents include, laurylmaltoside, Triton X-100, and Tween. Examples of zwitterionic detergents include 3-[(3-cholamidopropyl) dimthylammonio]propane-sulfonate (CHAPS), and N-tetradecyl-N,N-dimethyl-3-ammoniu-1-propanesulfonate.

Surface Tension

The surface tension of a liquid is the force acting over the surface of the liquid per unit length of surface that is perpendicular to the force that is acting of the surface. Surface charge has the units force per lengh, e.g. Newtons/meter.

Membrane Active Compound

Membrane active agents or compounds are compounds (typically a polymer, peptide or protein) that are able alter the membrane structure. This change in structure can be shown by the compound inducing one or more of the following effects upon a membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release. An example of a membrane active agent in our examples is the peptide melittin, whose membrane activity is demonstrated by its ability to release heme from red blood cells (hemolysis). In addition, dimethylmaleamic-modified mellitin (DM-Mel) reverts to melittin in the acidic environment of the endosome causes endosomal release as seen by the diffuse staining of fluorescein-labled dextran in our endosomal release assay.

More specifically membrane active compounds allow for the transport of molecules with molecular weight greater than 50 atomic mass units to cross a membrane. This transport may be accomplished by either the total loss of membrane structure, the formation of holes (or pores) in the membrane structure, or the assisted transport of compound through the membrane. In addition, transport between liposomes, or cell membranes, may be accomplished by the fusion of the two membranes and thereby the mixing of the contents of the two membranes.

Membrane Active Peptides.

Membrane active peptides are peptides that have membrane activity. There are many naturally occurring membrane active peptides such as cecropin (insects), magalnin, CPF 1, PGLa, Bombinin BLP-1 (all three from amphibians), melittin (bees), seminalplasmin (bovine), indolicidin, bactenecin (both from bovine neutrophils), tachyplesin 1 (crabs), protegrin (porcine leukocytes), and defensins (from human, rabbit, bovine, fingi, and plants). Gramicidin A and gramicidin S (bacillus brevis), the lantibiotics such as nisin (lactococcus lactis), androctonin (scorpion),cardiotoxin I (cobra), caerin (frog litoria splendida), dermaseptin (frog). Viral peptides have also been shown to have membrane activity, examples include hemagglutinin subunit HA-2 (influenza virus), E1 (Semliki forest virus), F1 (Sendai and measles viruses), gp41 (HIV), gp32 (SIV), and vp1 (Rhino, polio, and coxsackie viruses). In addition synthetic peptides have also been shown to have membrane activity. Synthetic peptides that are rich in leucines and lysines (KL or $KL_n$ motif) have been shown to have membrane activity. In particular, the peptide $H_2N$-KLLKLLLKLWLKLLKLLLKLL-$CO_2$, termed $KL_3$, is membrane active.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

The main chain of a polymer is composed of the atoms whose bonds are required for propagation of polymer length. For example in poly-L-lysine, the carbonyl carbon, a-carbon, and a-amine groups are required for the length of the polymer and are therefore main chain atoms. The side chain of a polymer is composed of the atoms whose bonds are not required for propagation of polymer length. For example in poly-L-lysine, the β, γ, δ, and ε-carbons, and ε-nitrogen are not required for the propagation of the polymer and are therefore side chain atoms.

To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" (M. P. Stevens Polymner Chemistry: An Introduction New York Oxford University Press 1990). Template polymerization can be used to form polymers from daughter polymers.

Step Polymerization

In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A-B yields -[A-B]-

Or the other approach is to have two difunctional monomers.

A-A+B-B yields -[A-A-B-B]-

Generally, these reactions can involve acylation or alkylation. Acylation is defined as the introduction of an acyl group (—COR) onto a molecule. Alkylation is defined as the introduction of an alkyl group onto a molecule. If functional group A is an amine then B can be (but not restricted to) an isothiocyanate, isocyanate, acyl azide, N-hydroxysuccininide, sulfonyl chloride, aldehyde (including formaldehyde and glutaraldehyde), ketone, epoxide, carbonate, imnidoester, carboxylate, or alkylphosphate, arylhalides (difluorodinitrobenzene), anhyderides or acid halides, p-nitrophenyl esters, onitrophenyl pentachlorophenyl esters, or pentafluorophenyl esters. In other terms when function A is an amine then function B can be acylating or alkylating agent or amination.

If functional group A is a thiol, sulfhydryl, then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) a diazoacetate or an amine in which a carbodiimide is used. Other additives may be utilized such as carbonyldiimidazole, dimethylaminopyridine, N-hydroxysaccinimide or alcohol using carbodiimide and dimethylaminopyridine.

If functional group A is an hydroxyl then function B be (but not restricted to) an epoxide, oxirane, or an amine in which carbonyldiimidazole or N, N'-disuccinimidyl carbonate, or N-hydroxysuccinimidyl chloroformate or other chlorofornates are used.

If functional group A is an aldehyde or ketone then function B can be (but not restricted to) an hydrazine, hydrazide derivative, amine (to form a imine or iminium that may or may not be reduced by reducing agents such as NaCNBIH) or hydroxyl compound to form a ketal or acetal. Yet another approach is to have one difunctional monomer so that A-A plus another agent yields -[A-A]-.

If function A is a thiol, sulfhydryl, group then it can be converted to disulfide bonds by oxidizing agents such as iodine ($I_2$) or $NaIO_4$ (sodium periodate), or oxygen ($O_2$). Function A can also be an amine that is converted to a thiol, sulfhydryl, group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives.

Reactions of the amine, hydroxyl, thiol sulfhydryl, carboxylate groups yield chemical bonds that are described as amide, amidine, disulfide, ethers, esters, enamine, ur ea, isothiourea, isourea, sulfonamide, carbamate, carbon-nitrogen double bond (imine), alkylamine bond (secondary amine), carbor itogen single bonds in which the carbon contains a hydroxyl group, thio-ether, diol, hydrazone, diazo, or sulfone.

Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, mcthacrylate, acrylamide, methaacrylamide groups can undergo chain reaction which can be radical, anionic, or cationic. Chain polymerization can also be accomplished by cycle or ring opening polymerization. Several different types of free radical initiatiors could be used that include peroxides, hydroxy peroxides, and azo compounds such as 2,2'-Azobis(-amidinopropane) dihydrochloride (AAP). A compound is a material made up of two or more elements.

Types of Monomers: A wide variety of monomers can be used in the polymerization processes. These include positive charged organic monomers such as amines, imidine, guanidine, imine, hydroxylamine, hydrozyine, heterocycles (like imidazole, pyridine, morpholine, pyrimidine, or pyrene. The amines could be pH-sensitive in that the pKa of the amine is within the physiologic range of 4 to 8. Specific amines include spermine, spermidine, N,N'-bis(2-aminoethyl)-1,3-propanediamine (AEPD), and 3,3'-Diamino-N,N-dimethyldipropylammonium bromide.

Monomers can also be hydrophobic, hydrophilic or amphipathic. Monomers can also be intercalating agents such as acridine, thiazole organge, or ethidium bromide.

Other Components of the Monomers and Polymers: The polymers have other groups that increase their utility. These groups can be incorporated into monomers prior to polymer formation or attached to the polymer after its formation. These groups include: Targeting Groups-such groups are used for targeting the polymernucleic acid complexes to specific cells or tissues. Examples of such targeting agents include agents that target to the asialoglycoprotein receptor by using asiologlycoproteins or galactose residues. Other proteins such as insulin, EGF, or trausferrin can be used for targeting. Protein refers to a molecule made up of 2 or more amino acid residues connected one to another as in a polypeptide. The amino acids may be naturally occurring or synthetic. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes.

The polymers can also contain cleavable groups within thermselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.
Polyelectrolyte A polyelectrolyte, or polyion, is a polymer possessing charge, that is the polymer contains a group (or groups) that has either gained or lost one or more electrons. A polycation is a polyelectrolyte possessing net positive charge, for example poly-L-lysine hydrobromide. The polycation can contain monomer units that are charge positive, charge neutral, or charge negative, however, the net charge of the polymer must be positive. A polycation also can mean a nonpolymeric molecule that contains two or more positive charges. A polyanion is a polyelectrolyte containing a net negative charge. The polyanion can contain monomer units that are charge negative, charge neutral, or charge positive, however, the net charge on the polymer must be negative. A polyanion can also mean a non-polymeric molecule that contains two or more negative charges. The term polyelectrolyte includes polycation, polyanion, zwitterionic polymers, and neutral polymers. The term zwitterionic refers to the product (salt) of the reaction between an acidic group and a basic group that are part of the same molecule.
Chelator A chelator is a polydentate ligand, a molecule that can occupy more than one site in the coordination sphere of an ion, particularly a metal ion, primary amine, or single proton. Examples of chelators include crown ethers, cryptates, and non-cyclic polydentate molecules. A crown ether is a cyclic polyether containing (—X-(CR1-2)n)m units, where n=1–3 and m=3–8. The X and CR1-2 moieties can be substituted, or at a different oxidation states. X can be oxygen, nitrogen, or sulfur, carbon, phosphorous or any combination thereof. R can be H, C, O, S, N, P. A subset of crown ethers described as a cryptate contain a second (—X-(CR1-2)n)z strand where z=3–8. The beginning X atom of the strand is an X atom in the (—X-(CR1-2)n)m unit, and the terminal CH2 of the new strand is bonded to a second X atom in the (—X-(CR1-2)n)m unit. Non-cyclic polydentate molecules containing (—X-(CR1-2)n)m unit(s), where n=1–4 and m=1–8. The X and CR1-2 moieties can be substituted, or at a different oxidation states. X can be oxygen, nitrogen, or sulfur, carbon, phosphorous or any combination thereof.
Polychelator A polychelator is a polymer associated with a plurality of chelators by an ionic or covalent bond and can include a spacer. The polymer can be cationic, anionic, zwitterionic, neutral, or contain any combination of cationic, anionic, zwitterionic, or neutral groups with a net charge being cationic, anionic or neutral, and may contain steric stabilizers, peptides, proteins, signals, or amphipathic compound for the formation of micellar, reverse micellar, or unilamellar structures. Preferably the amphipathic compound can have a hydrophilic segment that is cationic, anionic, or zwitterionic, and can contain polymerizable groups, and a hydrophobic segment that can contain a polymerizable group.
Steric Stabilizer A steric stabilizer is a hydrophilic group that prevents aggregation of a polymer or particle by sterically hindering particle to particle electrostatic interactions. Examples include: alkyl groups, PEG chains, polysaccharides, hydrogen molecules, alkyl amines. Electrostatic interactions are the noncovalent association of two or more substances due to attractive forces between positive and negative charges.
Buffers Buffers are made from a weak acid or weak base and their salts. Buffer solutions resist changes in pH when additional acid or base is added to the solution.
Biological, Chemical, or Biochemical Reactions Biological, chemical, or biochemical reactions involve the formation or cleavage of ionic and/or covalent bonds.
Reactive A compound is reactive if it is capable of forming either an ionic or a covalent bond with another compound. The portions of reactive compounds that are capable of forming covalent bonds are referred to as reactive functional groups.
Lipids Lipids are compounds that are insoluble in water but soluble in organic solvent which have the general structure composed of two distinct hydrophobic sections, that is two separate sections of uninterrupted carbon-carbon bonds. The two hydrophobic sections are connected through a linkage that contains at least one heteroatom, that is an atom that is not carbon (e.g. nitrogen, oxygen, silicon, and sulfur). Examples include esters and amides of fatty acids and include the glycerides (1,2-dioleoylglycerol (DOG)), glycolipids, phospholipids (dioleoylphosphatidylethanolamine (DOPE)).
Hydrocarbon Hydrocarbon means containing carbon and hydrogen atoms; and halohydrocarbon means containing carbon, halogen (F, Cl, Br, I), and hydrogen atoms.
Alkyl, Alkene, Alkyne, Aryl Alkyl means any $sp^3$-hybridized carbon-containing group; alkenyl means containing two or more $sp^2$ hybridized carbon atoms; aklkynyl means containing two or more sp hybridized carbon atoms; aralkyl mears containing one or more aromatic ring(s) in addition containing $sp^3$ hybridized carbon atoms; aralkenyl means containing one or more aromatic ring(s) in addition to containing two or more $sp^2$ hybridized carbon atoms; aralknyl means containing one or more aromatic ring(s) in addition to containing two or more sp hybridized carbon atoms; steroid includes natural and unnatural steroids and steroid derivatives.

Steroid

A steroid derivative means a sterol, a sterol in which the hydroxyl moiety has been modified (for example, acylated), or a steroid hormone, or an analog thereof. The modification can include spacer groups, linkers, or reactive groups.

Carbohydrate

Carbohydrates include natural and unnatural sugars (for example glucose), and sugar derivatives (a sugar derivative means a system in which one or more of the hydroxyl groups on the sugar moiety has been modified (for example, but not limited to, acylated), or a system in which one or more of the hydroxyl groups is not present).

Polyoxyethylene

Polyoxyethylene means a polymer having ethylene oxide units (—$(CH_2CH_2O)_{n-}$, where n=2–3000).

Compound

A compound is a material made up of two or more elements.

Electron Withdrawing and Donating Groups

Electron withdrawing group is any chemical group or atom composed of electronegative atom(s), that is atoms that tend to attract electrons. Electron donating group is any chemical group or atom composed of electropositive atom (s), that is atoms that tend to attract electrons.

Resonance Stabilization

Resonance stabilization is the ability to distribute charge on multiple atoms through pi bonds. The inductive effective, in a molecule, is a shift of electron density due to the polarization of a bond by a nearby electronegative or electropositive atom.

Activated Carboxylate

An activated carboxylate is a carboxylic acid derivative that reacts with nucleophiles to form a new covalent bond. Nucleophiles include nitrogen, oxygen and sulfur-containing compounds to produce ureas, amides, carbonates, carbamates, esters, and thioesters. The carboxylic acid may be activated by various agents including carbodiimides, carbonates, phosphoniums, uroniums to produce activated carboxylates acyl ureas, acylphosphonates, acid anhydrides, and carbonates. Activation cf carboxylic acid may be used in conjunction with hydroxy and amine-containing compounds to produce activated carboxylates N-hydroxysuccinimide esters, hydroxybenzotriazole esters, N-hydroxy-5-norbornene-endo-2,3-dicarboximide esters, p-nitrophenyl esters, pentafluorophenyl esters, 4-dimethylaminopyridinium amides, and acyl imidazoles.

Nucleophile

A nucleophile is a species possessing one or more electron-rich sites, such as an unshared pair of electrons, the negative end of a polar bond, or pi electrons.

Cleavage and Bond Breakage

Cleavage, or bond breakage is the loss of a covalent bond between two atoms. Cleavable means that a bond is capable of being cleaved.

Substituted Group or Substitution

A substituted group or a substitution refers to chemical group which is placed onto a parent system instead of a hydrogen atom. For the compound methylbenzene (toluene), the methyl group is a substituted group, substituent, or substitution on the parent system benzene. The methyl groups on 2,3-dimethylmaleic anhydride are substituted groups, or substitutions on the parent compound (or system) maleic anhydride.

Primary and Secondary Amine

A primary amine is a nitrogen-contaning compound which is derived by monosubstitution of ammonia ($NH_3$) by a carbon-containing group. A primary amine is a nitrogen-containing compound which is derived by disubstitution of ammonia ($NH_3$) by a carbon-containing group.

EXAMPLES

The following examples are provided in order to demonstrate and further illustrate certain preferred embodiments and aspects of the present invention and are not to be construed as limiting the scope thereof.

Example 1

Synthesis of Succinyl-β-cyclodextrin

β-Cyclodextrin (0.5 gm, 0.38 mmol) and succinic anhydride (0.5 gm, 5 mmol) were dissolved in anhydrous pyridine (10 mL) for 4 h. The succinyl-β-cyclodextrin was then precipitated by addition of 40 mL isopropyl alcohol. The precipitate was then washed 3 times with 10 mL isopropyl alcohol.

Example 2

Synthesis of Poly-L-lysine-succinyl-β-cyclodextrin

Succinyl-β-cyclodextrin (75 mg, 0.05 mmol) and poly-L-lysine (2 mg, MW 52,000, 0.01 mmol amines) were dissolved in 1 mL water. To this mixture was added N-(3-dimethylaminopropyl)-N'-ethylcarbodiimide hydrochloride (40 mg, 0.2 mnmol) and the reaction was allowed to proceed overnight. The reaction mixture was then placed into a dialysis bag (12,000 molecular weight cutoff) and dialyzed against 3×1 L water for 72 hr. Lyophilization resulted in 6.7 mg of poly-L-lysine-succinyl-β-cyclodextrin, which is 35% modification of the amine residues. The polymer was then dissolved in 0.2 mL of water.

Example 3

Synthesis of Oleoyl poly-L-lysine

Poly-L-lysine (5 mg, 0.02 mmol amines) was dissolved in 0.5 mL water, to this solution was added oleoyl chloride (0.5 mg, 0.002 mmol) in 20 µL of acetonitrile.

Example 3:

Synthesis of Succinyloleoylpoly-L-lysine

To a solution of poly-L-lysine-oleoyl amide (2 mg) in 200 mL water was added succinic anhydride (20 mg, 0.2 mmol) and potassium carbonate (100 mg 0.7 mmol). After 5 minutes, the succinylpoly-L-lysine-oleoyl amide was precipitated by addition of 1 mL isopropyl alcohol.

Example 3

Synthesis of Epichlorohydrin-β-cyclodextrin Copolymer

β-Cyclodextrin (0.5 gm, 0.38 mmol) and sodium hydroxide (0.18 gm, 4.5 mmol) were dissolved in water (0.8 mL) and heated to 30° C. To this solution was added epichlorohydrin (0.345 mL, 4.4 mmol) and the immiscible solutions were stirred at 30° C. for 3.5 h, during which time the epichlorohydrin dissolved in the aqueous solution. The epichlorohydrin-β-cyclodextrin copolymer was then precipitated by the addition of acetone (10 mL). The acetone was decanted and the precipitate was dissolved in water (20 mL) and dialyzed in 14,000 molecular weight cutoff tubing against 2×1L water for 48 h. The polymer was then isolated by lyophilization to yield 0.3 gm of polymer.

Example 4

Characterization of Particles Formed by Poly-L-lysine, Epichlorohydrin-β-cyclodextrin Copoyvmer, and 4-t-butylbenzoic Acid

To a solution of epichlorohydrin-β-cyclodextrin copolymer (100 μg/mL) and poly-L-lysine (100 μg/mL) was added 4-t-butylbenzoic acid (3 mM). The size of the particle formed by the three agents was 100 nm, measured by a Brookhaven ZetaPlus Particle Sizer. Particle formation is observed only in the presence of all three components and is independent of the order of addition of each component.

Examnple 5

Characterization of Particles Formed by Plasmid DNA, Epichlorohydrin-β-cyclodextrin Copolymer, and Oleoylamine

To a solution of epichlorohydrin-β-cyclodextrin copolymer (50 μg/mL) and plasmid DNA (10 μg/mL) was added oleoylamine (0.1 mM). The size of the particle formed by the three agents was 78 nm, measured by a Brookhaven ZetaPlus Particle Sizer. Particle formation is observed only in the presence of all three components and is independent of the order of addition of each component.

Example 6

Characterization of Particles Formed Between Plasmid DNA and Poly-L-lysine-succinyl-β-cyclodextrin

To a solution of plasmid DNA (10 μg/mL) was added poly-L-lysine-succinyl-β-cyclodextrin (30 μg/mL). The size of the particle formed was 88 run and its charge was 11±7 mV, measured by a Brookhaven ZetaPlus Particle Sizer. To these particle was added Triton X-100 (0.2 mg/mL) resulting in a particle that was 140 nm in size with a charge of 22±4 mV. Addition of sodium chloride (100 mM) to these particles resulted in particles that were 115 nm in size with a charge of 7±2 mV. If Triton x-100 is not added to the particles prior to the addition of sodium chloride the particles become large, >200 nm.

Example 7

In Vitro Transfection with DNA-poly-L-lysine-succinylpoly-L-lysine-oleoyl Amide Particles in the Presence of β-Cyclodextrin

To plasmid DNA pCIluc (10 μg/mL, 2.6 μg/μL pCIluc; prepared according to Danko I, Williams P, Herweijer H, Zhang G, Latendresse J S, Bock I, Wolff J A *Hum. Mol. Genet.* 1997, 6, 1435) in 0.5 mL of 0 or 3 mM aqueous β-cyclodextrin was added poly-Llysine (30 μg/mL). Subsequently, 0.15 mg/mL of succinyloleoylpoly-L-lysine was added. The DNA complexes were then added (200 μL) to a well containing 3T3 mouse embryonic fibroblast cells in 290 mM glucose and 5 mM HEPES buffer pH 7.5. After 1.5 h, the glucose solution was replaced with Dubelco's modified Eagle Media and the cells were allowed to incubate for 48 h. The cells were then harvested and then assayed for luciferase activity. Luciferase activity in the presence of β-cyclodextrin was 33-fold higher (324,305 relative light units) than in the absence of β-cyclodextrin (RLU=9,924).

Example 8

In Vitro Transfection with DNA-poly-L-lysine-epichlorohydrin-β-cyclodextrin Copolymer in the Presence of p-t-butyl-benzoic Acid

To plasmid DNA pCIluc (10 μg/mL, 2.6 μg/μL pCIluc) in 0.5 mL of aqueous 0 or 3 mM 4-t-butylbenzoic acid was added poly-L-lysine (30 μg/mL). Subsequently, 0.15 mg/mL of succinylated poly-L-lysine or epichlorohydrin-β-cyclodextrin copolymer was added. The DNA complexes were then added (200 μL) to a well containing 3T3 mouse embryonic fibroblast cells in Dubelco's modified Eagle Media. After 1.5 h, the media was changed and the cells were allowed to incubate for 48 h. The cells were then harvested and then assay for luciferase activity. Luciferase activity for the particles composed of epichlorohydrin-β-cyclodextrin copolymer was 81-fold higher (314166 relative light units(RLU)) than those particles composed of succinylated poly-L-lysine (3868 RLU).

Example 9

Characterization of Complexes of Plasmid DNA, Dodecylamine, and β-cyclodextrin-epichlorohydrin Copolymer

To a solution of plasmid DNA (10 μg/mL) and β-cyclodextrin-epichlorohydrin copolymer (50 μg/mL) was added dodecylamine (100 μM). The size of the particle formed was 181 nm as measured by a Brookhaven ZetaPlus Particle Sizer. Prior to the addition of dodecylamine there were no particles formed and solutions of β-cyclodextrin epichlorohydrin copolymer and dodecyl amine do no not form particles.

Example 10

Characterization of Complexes of Plasmid DNA. 1-adamantamine, and β-cyclodextrin-epichlorohydrin Copolymer

To a solution of plasind DNA (10 μg/mL) and β-cyclodextrin-epichlorohydrin copolymer (50 μmL) was added various amounts of 1-adamantanamine (100–600 μM). The size of the particle formed was 181 nm as measured by a Brookhaven ZetaPlus Particle Sizer. Prior to the addition of dodecylamine there were no particles formed and solutions of β-cyclodextrin epichlorohydrin copolymer and dodecyl amine do no not form particles.

| [1-adamantamine] (μM) | Size of particles (nm) |
| --- | --- |
| 100 | >30,000 |
| 200 | 125 |
| 300 | 85 |
| 400 | 78 |

Example 11

In Vivo Expression of Complexes of Plasmid DNA, 1-adamantamine, and β-cyclodextrin-epichlorohydrin Copolymer

A complex of pCI Luc (50 μg/mL), 250 μg/mL β-cyclodextrin-epichlorohydrin copolymer, and 6 mM aantamine in 0.2 mL were diluted to 2.5 mL in Ringers solution. Tail vein injections of 2.5 mL of the complex were performed as previously described (Zhang, G., Budker, V., Wolff, J. A. Hum. Gene Ther. 1999, 10, 1735.) Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468,1990.). A Lumat LB 9507 (EG&G Berthold, BadWildbad, Germany) luminometer was used.

| Organ | Relative Light Units |
|---|---|
| Liver | 10,340,000 |
| Spleen | 103,631 |
| Lung | 102,851 |
| Heart | 50,350 |
| Kidney | 261,912 |

Example 12

In Vivo Expression of Complexes of Digoxin-labeled Plasmid DNA and γ-cyclodextrin

Plasmid DNA was labeled with Mirus' LabelIt® digoxin labeling kit according to protocol. A complex of digoxin-labeled pCI Luc (2 μg) and γ-cylodextrin (17 mg) were formulated in 2.5 mL in Ringers solution. Tail vein injections of the complex were performed as previously described (Zhang, G., Budker, V., Wolff, J. A. Hum. Gene Ther. 1999, 10, 1735.) Luciferase expression was determined as previously reported (Wolff, J. A., Malone, R. W., Williams, P., Chong, W., Acsad, G., Jani, A. and Felgner, P. L. Direct gene transfer into mouse muscle in vivo. Science, 1465–468, 1990.). A Lumat LB 9507 (EG&G Berthold, Bad-Wildbad, Germany) luminometer was used.

| Organ | Relative Light Units |
|---|---|
| Liver | 9,450,000 |
| Spleen | 365,000 |
| Lung | 290,000 |
| Heart | 111,000 |
| Kidney | 166,000 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cell biology, chemistry, molecular biology, biochemistry or related fields are intended to be within the scope of the following claims.

We claim:

1. A process for obtaining an expression product by delivering a polynucleotide to a cell, comprising:
   a) associating a noncovalent amphiphilic polyelectrolyte a cyclodextrin, and a polynucleotide thereby forming a complex, wherein the noncovalent amphiphilic polyelectrolyte consists of an polymeric amphiphile binding agent and charged amphiphiles;
   b) delivering the complex to the cell; and,
   c) expressing the polynucleotide.

2. The process of claim 1 further comprising complexing the polynucleotide with a polycation.

3. The process of claim 1 further comprising associating a polyanion in step (a).

4. The process of claim 1 wherein the amphiphile consists of an interaction modifier.

5. The process of claim 1 wherein the cell is in a mammal.

6. The process of claim 1 wherein the polynucleotide consists of DNA.

7. The process of claim 1 wherein the polynucleotide consists of a gene.

8. A complex for delivering and expressing DNA in a mammal, comprising: a noncovalent amphiphilic polyelectrolyte a cyclodexin, and DNA in complex, wherein the noncovalent amphiphilic polyelectrolyte consists of an polymeric amphiphile binding agent and charged amphiphiles.

9. The complex of claim 8 wherein the amphiphile is attached to the DNA.

10. The complex of claim 9 wherein the amnphiphile is covalently attached to DNA.

11. The complex of claim 8 wherein the amphiphile binding agent consists of a cyclodextrin.

12. A process for obtaining an expression product in vivo, comprising:
    a) forming a complex with a noncovalent amphiphilic polyelectrolyte and a polynucleotide wherein the noncovalent amphiphilic polyelectrolyte consists of a polycyclodextrin and charged amphiphiles;
    b) delivering the complex to a cell in a mammal;
    c) expressing the polynucleotide.

13. The process of claim 12 further comprising complexing the polynucleotide with a polycation.

14. The process of claim 12 further comprising associating a polyanion in step (a).

15. The process of claim 12 wherein the amphiphile consists of an interaction modifier.

* * * * *